United States Patent [19]

Kiehs et al.

[11] Patent Number: 4,692,187
[45] Date of Patent: Sep. 8, 1987

[54] ISOUREAS AND THEIR USE FOR CONTROLLING UNDESIRABLE PLANT GROWTH

[75] Inventors: Karl Kiehs, Lampertheim; Bruno Würzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 825,627

[22] Filed: Feb. 3, 1986

[30] Foreign Application Priority Data

Feb. 9, 1985 [DE] Fed. Rep. of Germany ....... 3504453

[51] Int. Cl.$^4$ ..................... C07C 127/26; A01N 47/42
[52] U.S. Cl. ........................................... 71/107; 558/8; 71/108; 71/109; 71/110; 71/111; 71/112; 71/119; 71/120; 71/121
[58] Field of Search ..................... 558/8; 71/121, 107, 71/108, 109, 110, 111, 112, 119, 120

[56] References Cited

FOREIGN PATENT DOCUMENTS 222131 7/1962 Austria .
1138039 10/1962 Fed. Rep. of Germany .
940663 10/1963 United Kingdom .

Primary Examiner—Paul J. Killos
Assistant Examiner—L. Hendriksen
Attorney, Agent, or Firm—Keil & Weinkauf

[57] ABSTRACT

Isoureas of the formula

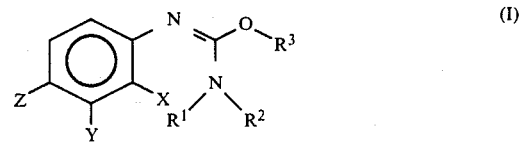

where X, Y and Z are each hydrogen, halogen, alkyl, alkoxy, haloalkyl, unsubstituted or substituted phenoxy or unsubstituted or substituted arylalkoxy, $R^1$ is alkyl, $R^2$ is alkyl or methoxy and $R^3$ is benzyl or is phenyl which can be monosubstituted or polysubstituted by alkyl, halogen, alkoxy, haloalkoxy, hydroxyl, nitro, alkoxycarbonylmethoxy, alkoxycarbonylethoxy or a radical—NH—$R^4$, processes for their preparation, and their use for controlling undesirable plant growth.

8 Claims, No Drawings

ISOUREAS AND THEIR USE FOR CONTROLLING UNDESIRABLE PLANT GROWTH

The present invention relates to novel isoureas, their preparation, herbicides which contain these compounds as active ingredients, and their use for controlling undesirable plant growth.

Isoureas which can be used as herbicides are disclosed in German Pat. No. 1,137,000. This patent describes only a few compounds whose herbicidal action is restricted to preemergence application.

We have found that isoureas of the formula I

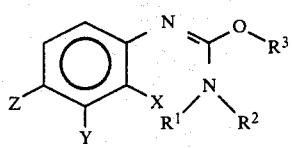

where X, Y and Z are identical or different and are each hydrogen, halogen, $C_1$–$C_4$-alkyl, $C_1$–$C_4$-alkoxy or $C_1$–$C_3$-haloalkyl, or are each phenoxy which is unsubstituted or substituted by halogen or $C_1$–$C_4$-alkyl, or are each aryl-$C_1$–$C_4$-alkoxy, where the aryl radical may be alkylated, $R^1$ is $C_1$–$C_3$-alkyl, $R^2$ is $C_1$–$C_3$-alkyl or methoxy, $R^3$ is benzyl or is phenyl which can be monosubstituted or polysubstituted by $C_1$–$C_5$-alkyl, halogen, $C_1$–$C_4$-alkoxy, $C_1$–$C_3$-haloalkoxy, nitro, hydroxyl, $C_2$- or $C_3$-alkoxycarbonylmethoxy, 1-($C_2$- or $C_3$-alkoxycarbonyl)-ethoxy or a radical -NH-$R^4$, where $R^4$ is $C_2$–$C_4$-alkoxycarbonyl, $C_2$–$C_4$-alkylcarbonyl, $C_4$–$C_7$-cycloalkylcarbonyl, N-($C_1$–$C_4$-alkyl)-N-($C_1$–$C_4$-alkoxy)-aminocarbonyl, N,N-di-($C_1$–$C_4$-alkyl)-aminocarbonyl or $C_2$–$C_3$-alkoxycarbonyl-$C_1$–$C_4$-alkyl, possess very good herbicidal activity, particularly in the post-emergence method, and are superior to known active ingredients of similar structure.

In formula I, X, Y and Z are each hydrogen, halogen, e.g. chlorine or fluorine, straight-chain or branched $C_1$–$C_4$-alkyl, e.g. methyl, ethyl, isopropyl or tert.-butyl, straight-chain or branched $C_1$–$C_4$-alkoxy, e.g. methoxy, ethoxy or isopropoxy, straight-chain or branched $C_1$–$C_3$ haloalkyl, e.g. trifluoromethyl, aryl-$C_1$–$C_4$-alkoxy, where the aryl radical can carry $C_1$–$C_4$-alkyl groups, such as methyl, e.g. 2-(4-methylphenyl)-ethoxy, 2-(4-ethylphenyl)-ethoxy, 2-(3,4-dimethylphenyl)-ethoxy or 2-(4-n-propylphenyl)-ethoxy, or phenoxy which is unsubstituted or substituted by halogen or $C_1$–$C_4$-alkyl, e.g. 4-chlorophenoxy, 4-fluorophenoxy, 4-bromophenoxy, 3,4-dimethylphenoxy, 4-isopropylphenoxy or 4-tert.-butylphenoxy, $R^1$ is straight-chain or branched $C_1$–$C_3$-alkyl, e.g. methyl, ethyl or isopropyl, preferably methyl, $R^2$ is straight-chain or branched $C_1$–$C_3$-alkyl, e.g. methyl, ethyl or isopropyl, preferably methyl or methoxy, $R^3$ is phenyl which can be monosubstituted or disubstituted by straight-chain or branched alkyl, such as methyl, ethyl or isopropyl, halogen, such as fluorine, chlorine or bromine, straight-chain or branched $C_1$–$C_4$-alkoxy, such as methoxy, tert.-butoxy or isopropoxy, straight-chain or branched $C_1$–$C_3$-haloalkoxy, such as trifluoromethoxy, 1,1,2,2-tetrafluoroethoxy, 1,1,2-trifluoro-2-chloroethoxy or 1,1,2-trifluoro-2-bromoethoxy, nitro, hydroxyl, $C_2$- or $C_3$-alkoxycarbonylmethoxy, 1-($C_2$- or $C_3$-alkoxycarbonyl)-ethoxy, such as methoxycarbonylmethoxy, ethoxycarbonylmethoxy, 1-methoxycarbonylethoxy or 1-ethoxycarbonylethoxy, or a radical of the formula -NHR$^4$, and R$^4$ is straight-chain or branched $C_2$–$C_4$-alkoxycarbonyl, N-($C_1$–$C_4$-alkyl)-$C_2$–$C_4$-alkylcarbonyl, $C_4$–$C_7$-cycloalkylcarbonyl, N-($C_1$–$C_4$-alkoxy)-aminocarbonyl, N,N-di-($C_1$–$C_4$-alkyl)-aminocarbonyl or $C_2$- or $C_3$-alkoxy-carbonyl-$C_1$–$C_4$alkyl, e.g. methoxycarbonyl, ethoxycarbonyl, isopropoxycarbonyl, n-butoxycarbonyl, methylcarbonyl, ethylcarbonyl, n-propylcarbonyl, tert.-butylcarbonyl, cyclopropylcarbonyl, cyclopentylcarbonyl, cyclohexylcarbonyl, dimethylaminocarbonyl, diethylaminocarbonyl, di-n-propylaminocarbonyl, N-methyl-N-propylaminocarbonyl, methoxycarbonylmethyl, 2-methoxycarbonylethyl, 2-ethoxycarbonylethyl, ethoxycarbonylmethyl, 3-methoxycarbonylpropyl, 3-ethoxycarbonylpropyl, propoxycarbonylmethyl, di-n-butylaminocarbonyl, di-i-propylaminocarbonyl, N-methyl-N-methoxyaminocarbonyl.

Examples of radicals $R^3$ are phenyl, 2-fluorophenyl, 4-fluorophenyl, 3-fluorophenyl, 2-chlorophenyl, 3-chlorophenyl, 4-chlorophenyl, 2,4-dichlorophenyl, 3,4dichlorophenyl, 3,5-dichlorophenyl, 4-bromophenyl, 2,4-difluorophenyl, 2-bromo-4-chlorophenyl, 2-methylphenyl, 3,4-dimethylphenyl, 4-isopropylphenyl, 2-chloro-4,5-dimethylphenyl, 4-tert.-butylphenyl, 3-isopropylphenyl, 2-isopropylphenyl, 2-sec.-butylphenyl, 3-sec.-butylphenyl, 2-methyl-4-chloro-5-isopropylphenyl, 2-methoxyphenyl, 3-methoxyphenyl, 4-methoxyphenyl, 3,4-dimethoxyphenyl, 2-isopropoxyphenyl, 4-isopropoxyphenyl, 4-tert.-butoxyphenyl, 2-trifluorophenyl, 3-trifluorophenyl, 4-trifluorophenyl, 3-hydroxyphenyl, 4-hydroxyphenyl, 3-(N,N-dimethylcarbamylamino)-phenyl, 4-(N,N-dimethylcarbamylamino)-phenyl, 2-chloro-4-(N,N-dimethylcarbamylamino)-phenyl, 2-fluoro-4-(N,N-dimethylcarbamylamino)-phenyl, 2-methyl-4-(N,N-dimethylcarbamylamino)-phenyl, 2,6-dichloro-4-N,N-dimethylcarbamylamino)-phenyl, 2-methyl-5-(N,N-dimethyl-carbamylamino)-phenyl, 2-chloro-5-(N,N-dimethylcarbamylamino)-phenyl, 2-fluoro-5-(N,N-dimethylcarbamylamino)-phenyl, 3-(N-methyl-N-methoxycarbamylamino)-phenyl, 4-methyl-N-methoxycarbamylamino)-phenyl, 2-chloro-4-(N-methyl-N-methoxycarbamylamino)-phenyl, -fluoro-4-(N-methyl-N-methoxycarbamylamino)-phenyl, 2-methyl-4-(N-methyl-N-methoxycarbamylamino)-phenyl, 2-chloro-5-(N-methyl-N-methoxycarbamylamino)-phenyl, 2-methyl-5-(N-methyl-N-methoxycarbamylamino)-phenyl, 3-(N,N-diethylcarbamylamino)-phenyl, 4-(N,N-diethylcarbamylamino)-phenyl, 2,6-dichloro-4-(N,N-dimethylcarbamylamino)-phenyl, 2,6-dichloro-4-(N-methyl-N-methoxycarbamylamino)-phenyl, 2-acetylamino-phenyl, 3-acetylaminophenyl, 4-acetylaminophenyl, 2-propionylaminophenyl, 3-propionylamino, 4-propionylaminophenyl, 2-pivaloylaminophenyl, 3-pivaloylaminophenyl, 4-pivaloylaminophenyl, 2-chloro-4-acetylaminophenyl, 2-chloro-4-pivaloylaminophenyl, 2-chloro-4-propionylaminophenyl, 2-chloro-5-propionylaminophenyl, 2-chloro-5-acetylaminophenyl, 3-cyclopropylcarbonylaminophenyl, 4-cyclopropylcarbonylaminophenyl, 3-cyclopentylcarbonylaminophenyl, 4-cyclopentylcarbonylaminophenyl, 2-chloro-4-cyclopropylcarbonylaminophenyl, 2-chloro-5-cyclopropylcarbonylaminophenyl, 2-methyl-4-cyclopropylcarbonylaminophenyl, 2-methyl-5-cyclopropylcarbonylaminophenyl, 2-cyclohexylcarbonylaminophenyl, 3-cyclohexylcarbonylaminophenyl, 4-cyclohexylcarbonylaminophenyl, 2-chloro-4-cyclohexylcarbonylaminophenyl, 2-fluoro-4-cyclopropylcarbonylaminophenyl, 2-fluoro-5-cyclopropylcarbonylaminophenyl, 2-fluoro-5-cyclohexylcarbonylaminophenyl, 2,6-dichloro-4-cyclopropylcarbonylaminophenyl, 2,6-dichloro-4-cyclohexylcarbonylaminophenyl, 2-methoxycarbonylaminophenyl, 2-isopropoxycarbonylaminophenyl, 2-ethoxycarbonylaminophenyl, 3-methoxycarbonylaminophenyl, 3-ethoxycarbonylaminophenyl, 4-ethoxycarbonylaminophenyl, 4-n-butoxycarbonylaminophenyl, 4-tert.-butoxycarbonylaminophenyl, 2-chloro-4-ethoxycarbonylaminophenyl, 2-chloro-5-ethoxycarbonylaminophenyl, 2-bromo-5-ethoxycarbonylaminophenyl, 2-fluoro-5-ethoxycarbonylaminophenyl, 4-nitrophenyl, 3-nitrophenyl, 2-nitrophenyl, 2-chloro-4-nitrophenyl.

There are several possible synthesis routes for the preparation of the isoureas of the formula I:

1. The isoureas of the formula I are obtained
   (a) by reacting an aryl N-arylchloroformimidate of the formula

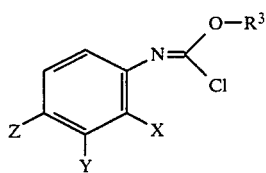

where X, Y, Z and $R^3$ have the above meanings, with an amine of the formula III

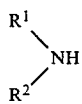

where $R^1$ and $R^2$ have the above meanings, or (b) by reacting a chloroformamidine of the formula IV

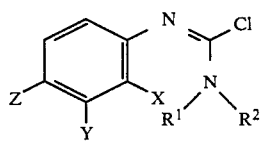

where X, Y, Z, $R^1$ and $R^2$ have the above meanings, with a phenol of the formula (V)

$R^3OH$            (V)

where $R^3$ has the above meanings, in the presence of an acid acceptor.

The aryl N-arylchloroformimidates of the formula II can be prepared by reacting an aryl isocyanide dichloride with a phenolate, for example a sbdium phenolate of the formula $NaOR^3$ (Houben-Weyl, Methoden der org. Chemie, vol. E 4, page 544 et seq. (1983)).

The chloroformamidines of the formula IV can be obtained by reacting a trisubstituted urea or thiourea with a chlorinating agent, such as $PCl_5$ or $COCl_2$ (Houben-Weyl, Methoden der org. Chemie, vol. E 4, page 555 et seq. (1983)). When $R^1$ and $R^2$ in the chloroformamidines of the formula IV are each alkyl, preferably methyl, it may be advantageous to prepare the chloroformamidines starting from phosgeneiminium chloride, according to the following equation:

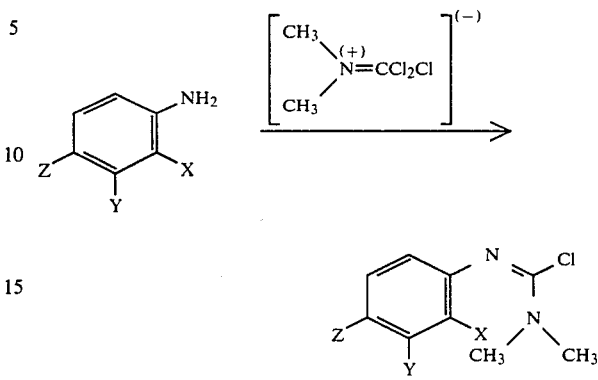

(Houben-Weyl, Methoden der org. Chemie, vol. E 4, page 558 (1983)).

The process selected is determined from case to case by industrial availability. It is particularly advantageous to prepare the isoureas of the formula I from chloroformamidines of the formula IV, which are obtained by reacting a trisubstituted urea derivative of the formula

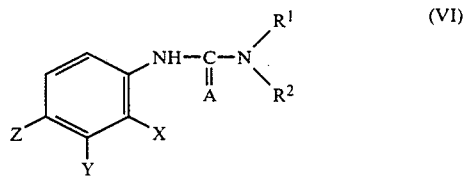

where A is oxygen or sulfur and X, Y, Z, $R^1$ and $R^2$ have the above meanings, with a chlorinating agent. The chloroformamidines IV are preferably reacted with the phenols of the formula $R^3$-OH in a ratio of from 1:1 to 1:1.4.

The reactions for the preparation of the isoureas of the formula I are advantageously carried out in a solvent or diluent which is inert to the reactants. Examples of substances which are suitable for this purpose are aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, ethers, such as diethyl ether, di-n-butyl ether, methyl tert.-butyl ether, tetrahydrofuran or dioxane, ketones, e.g. acetone, methyl ethyl ketone or methyl isopropyl ketone, nitriles, such as acetonitrile or propionitrile, and amides, such as N-methylpyrrolidone or dimethylformamide. Mixtures of these solvents or diluents may also be used.

The basic agents conventionally employed for the acylation of hydroxy compounds can be used as acid acceptors. Alkali metal carbonates and alcoholates, such as sodium carbonate, potassium carbonate and potassium tert-butylate, and aliphatic, aromatic and heterocyclic amines, e.g. triethylamine, piperidine, dimethylaniline, dimethylbenzylamine and pyridine, have proven particularly suitable.

Instead of carrying out the reaction in the presence of an acid acceptor, it is also possible first to prepare the salts, for example the alkali metal, alkaline earth metal or ammonium salts of the phenols of the formula $R^3OH$, and then to react these further with the compound of the formula III.

The processes for the preparation of the isoureas of the formula I can be carried out continuously or batchwise under atmospheric or superatmospheric pressure; for the sake of simplicity, atmospheric pressure is preferably employed.

The reaction temperature can be varied within a relatively wide range, but is in general about 0°–120° C., preferably 20°–50° C. Since the reaction is exothermic in some cases, it may be advantageous to employ external cooling at the beginning of the reaction.

To complete the reaction, the reaction mixture is stirred for a further 15 minutes to 24 hours, preferably from 1 hour to 5 hours, after which, depending on the solvent, the mixture is washed directly with water or the solvent is distilled off, and the residue is treated in a water-immiscible solvent and water. In any case, the organic layer is evaporated down after phase separation, and the product obtained as the residue can, if required, be purified by recrystallization or column chromatography.

The Examples which follow illustrate the preparation of the isoureas of the formula I.

EXAMPLE 1

10.4 g (0.05 mole) of phosphorus pentachloride and 11.6 g (0.05 mole) of N,N-dimethyl-N'-(3,4-dichlorophenyl)-urea in 75 ml of toluene are refluxed for 3 hours. After the volatile components have been distilled off under 0.1 mm Hg, 12.6 g of N,N-dimethyl-N'-(3,4-dichlorophenyl)-chloroformamidine are obtained in the form of an oil ($N_D25$: 1.6133).

|  | C | H | N | Cl |
|---|---|---|---|---|
| Calculated | 42.97 | 3.7 | 11.1 | 42.28 |
| Found | 42.7 | 3.7 | 10.6 | 42.7 |

12.6 g (0.05 mole) of N,N-dimethyl-N'-(3,4-dichlorophenyl)-chloroformamidine are added to 9.8 g (0.05 mole) of methyl 2-(4-hydroxyphenoxy)-propionate in 75 ml of dry dimethylformamide, after which 5.6 g (0.05 mole) of potassium tert.-butylate are introduced a little at a time at from 10° to 20° C., the mixture is then stirred for 2 hours at 50° C., the solvent is then distilled off under 10 mm Hg, and the residue is treated with methylene chloride/water. The methylene chloride solution is dried over sodium sulfate and then evaporated down to give an oily residue which is purified over a silica gel column using a 1:1 toluene/ethyl acetate mixture. 14.6 g of N,N-dimethyl-N'-(3,4-dichlorophenyl)-0-[4-(1-methoxycarbonyl)eth-1-yloxy]-phenylisourea ($n_D25 = 1.5732$) remain.

|  | C | H | N | Cl |
|---|---|---|---|---|
| Calculated | 55.5 | 4.9 | 6.81 | 17.2 |
| Found | 55.8 | 5.0 | 6.4 | 17.0 |

The following isoureas of the formula I are preferred by a similar method:

|  | $R^1$ | $R^2$ | $R^3$ | X | Y | Z | M.p. [°C.]/$n^{20}_D$ |
|---|---|---|---|---|---|---|---|
| 1 | CH$_3$ | CH$_3$ | 4-[(CH$_3$)$_2$NCO—NH]C$_6$H$_4$ | H | Cl | Cl | 137–139 |
| 2 | CH$_3$ | OCH$_3$ | 4-[(CH$_3$)$_2$NCO—NH]C$_6$H$_4$ | H | Cl | Cl | 140–142 |
| 3 | CH$_3$ | OCH$_3$ | 4-[(CH$_3$)$_2$NCO—NH]C$_6$H$_4$ | H | Cl | CH$_3$ | 121–122 |
| 4 | CH$_3$ | OCH$_3$ | 4-[(CH$_3$)$_2$NCO—NH]C$_6$H$_4$ | H | CF$_3$ | H |  |
| 5 | CH$_3$ | OCH$_3$ | 4-[(CH$_3$)$_2$NCO—NH]C$_6$H$_4$ | H | H | F |  |
| 6 | CH$_3$ | OCH$_3$ | 4-[(CH$_3$)$_2$NCO—NH]C$_6$H$_4$ | H | H | H | 147 |
| 7 | CH$_3$ | CH$_3$ | 4-[(CH$_3$)$_2$NCO—NH]C$_6$H$_4$ | H | H | 4-chlorophenoxy |  |
| 8 | CH$_3$ | CH$_3$ | 4-[(CH$_3$)(CH$_3$O)N—CO—NH]C$_6$H$_4$ | H | Cl | Cl | 104–105 |
| 9 | CH$_3$ | OCH$_3$ | 4-[(CH$_3$)(CH$_3$O)N—CO—NH]C$_6$H$_4$ | H | Cl | Cl | 93–96 |
| 10 | CH$_3$ | OCH$_3$ | 4-[(CH$_3$)(CH$_3$O)N—CO—NH]C$_6$H$_4$ | H | Cl | CH$_3$ |  |
| 11 | CH$_3$ | CH$_3$ | 4-[(CH$_3$)(CH$_3$O)N—CO—NH]C$_6$H$_4$ | H | CF$_3$ | H | 122–124 |
| 12 | CH$_3$ | OCH$_3$ | 4-[(CH$_3$)(CH$_3$O)N—CO—NH]C$_6$H$_4$ | H | H | H | 1.5780 |
| 13 | CH$_3$ | OCH$_3$ | 4-[(CH$_3$)(CH$_3$O)N—CO—NH]C$_6$H$_4$ | H | H | 2-(4-methyl-phenyl)-ethoxy | 1.5880 |

-continued

| | $R^1$ | $R^2$ | $R^3$ | X | Y | Z | M.p. [°C.]/$n^{20}_D$ |
|---|---|---|---|---|---|---|---|
| 14 | CH₃ | CH₃ | 4-C₂H₅CONHC₆H₄ | H | Cl | Cl | 1.6008 |
| 15 | CH₃ | OCH₃ | 4-C₂H₅CONHC₆H₄ | H | Cl | Cl | 1.5938 |
| 16 | CH₃ | OCH₃ | 4-C₂H₅CONHC₆H₄ | H | Cl | CH₃ | 1.5770 |
| 17 | CH₃ | CH₃ | 4-C₂H₅OCONHC₆H₄ | H | H | i-C₃H₇ | |
| 18 | CH₃ | CH₃ | 4-C₂H₅OCONHC₆H₄ | F | H | H | |
| 19 | CH₃ | CH₃ | 4-C₂H₅OCONHC₆H₄ | H | H | 4-chlorophenoxy | |
| 20 | CH₃ | CH₃ | 4-C₂H₅OCONH—C₆H₄ | H | Cl | Cl | 98–100 |
| 21 | CH₃ | OCH₃ | 4-C₂H₅OCONH—C₆H₄ | H | Cl | Cl | 96–97 |
| 22 | CH₃ | OCH₃ | 4-C₂H₅OCONH—C₆H₄ | H | Cl | CH₃ | 1.5780 |
| 23 | CH₃ | OCH₃ | 4-C₂H₅OCONH—C₆H₄ | H | CF₃ | H | |
| 24 | CH₃ | CH₃ | 4-C₂H₅OCONH—C₆H₄ | H | H | 2-(4-methyl-phenyl)-ethoxy | |
| 25 | CH₃ | CH₃ | 4-C₂H₅OCONH—C₆H₄ | H | H | i-C₃H₇ | |
| 26 | CH₃ | CH₃ | 4-[CH₃OCO—CH(CH₃)O]—C₆H₄ | H | Cl | Cl | 1.5732 |
| 27 | CH₃ | OCH₃ | 4-[CH₃OCO—CH(CH₃)O]—C₆H₄ | H | Cl | CH₃ | 1.5582 |
| 28 | CH₃ | CH₃ | 4-[CH₃OCO—CH(CH₃)O]—C₆H₄ | H | CF₃ | H | 1.5228 |
| 29 | CH₃ | CH₃ | 4-[CH₃OCO—CH(CH₃)O]—C₆H₄ | H | H | i-C₃H₇ | |
| 30 | CH₃ | CH₃ | 4-[CH₃OCO—CH(CH₃)O]—C₆H₄ | H | F | H | |
| 31 | CH₃ | CH₃ | 4-[CH₃OCO—CH(CH₃)O]—C₆H₄ | H | H | 4-chlorophenoxy | |
| 32 | CH₃ | CH₃ | 3-CH₃O—C₆H₄ | H | Cl | Cl | 1.6080 |
| 33 | CH₃ | CH₃ | 4-CH₃O—C₆H₄ | H | Cl | Cl | 72–74 |
| 34 | CH₃ | CH₃ | 4-t-C₄H₉O—C₆H₄ | H | Cl | Cl | |
| 35 | CH₃ | CH₃ | 4-t-C₄H₉O—C₆H₄ | H | CF₃ | H | |
| 36 | CH₃ | CH₃ | 4-t-C₄H₉O—C₆H₄ | H | H | i-C₃H₇ | |
| 37 | CH₃ | CH₃ | 3-CH₃OCONH—C₆H₄ | H | Cl | Cl | 1.5985 |
| 38 | CH₃ | OCH₃ | 3-CH₃OCONH—C₆H₄ | H | Cl | Cl | 109 |
| 39 | CH₃ | OCH₃ | 3-CH₃OCONH—C₆H₄ | H | CF₃ | H | 1.5340 |
| 40 | CH₃ | OCH₃ | 3-(CH₃)₂NCONH—C₆H₄ | H | Cl | Cl | 115–116 |
| 41 | CH₃ | OCH₃ | 3-(CH₃)₂NCONH—C₆H₄ | H | CF₃ | H | 1.5360 |
| 42 | CH₃ | CH₃ | 3-(CH₃)₂NCONH—C₆H₄ | H | H | 4-chlorophenoxy | |
| 43 | CH₃ | CH₃ | 3-(CH₃)₂NCONH—C₆H₄ | H | Cl | CH₃ | |
| 44 | CH₃ | CH₃ | 3-(CH₃)₂NCONH—C₆H₄ | H | H | F | |
| 45 | CH₃ | CH₃ | 2-CH₃—5-[(CH₃)₂N—CONH]—C₆H₃ | H | Cl | Cl | 132–134 |
| 46 | CH₃ | OCH₃ | 2-CH₃—5-[(CH₃)₂N—CONH]—C₆H₃ | H | Cl | Cl | 1.5843 |
| 47 | CH₃ | OCH₃ | 2-CH₃—5-[(CH₃)₂N—CONH]—C₆H₃ | H | CF₃ | H | 133–135 |
| 48 | CH₃ | OCH₃ | 2-CH₃—5-[(CH₃)₂N—CONH]—C₆H₃ | H | H | H | |
| 49 | CH₃ | CH₃ | 3-Cyclo-C₃H₅—CONH—C₆H₄ | H | Cl | Cl | 54–56 |
| 50 | CH₃ | CH₃ | 2-Cl—4-[CH₃N(OCH₃)CONH]—C₆H₃ | H | Cl | Cl | 1.5915 |
| 51 | CH₃ | OCH₃ | 2-Cl—4-[CH₃N(OCH₃)CONH]—C₆H₃ | H | Cl | Cl | 1.5830 |
| 52 | CH₃ | OCH₃ | 2-Cl—4-[CH₃N(OCH₃)CONH]—C₆H₃ | H | H | H | 1.5675 |
| 53 | CH₃ | CH₃ | 2-Cl—4-[CH₃N(OCH₃)CONH]—C₆H₃ | H | CF₃ | H | |
| 54 | CH₃ | OCH₃ | 2-Cl—4-[CH₃N(OCH₃)CONH]—C₆H₃ | H | CF₃ | H | |
| 55 | CH₃ | CH₃ | 2-CH₃—5-[CH₃N(OCH₃)CONH]—C₆H₃ | H | Cl | Cl | 127–129 |
| 56 | CH₃ | OCH₃ | 2-CH₃—5-[CH₃N(OCH₃)CONH]—C₆H₃ | H | Cl | Cl | 1.5740 |
| 57 | CH₃ | OCH₃ | 2-CH₃—5-[CH₃N(OCH₃)CONH]—C₆H₃ | H | CF₃ | H | |
| 58 | CH₃ | CH₃ | 2,6-Cl₂—4-[CH₃N(OCH₃)CONH]—C₆H₂ | H | Cl | Cl | 1.5895 |
| 59 | CH₃ | CH₃ | 2,6-Cl₂—4-[CH₃N(OCH₃)CONH]—C₆H₂ | H | CF₃ | H | |
| 60 | CH₃ | CH₃ | 2,6-Cl₂—4-[CH₃N(OCH₃)CONH]—C₆H₂ | H | H | H | |
| 61 | CH₃ | OCH₃ | 2-Cl—4-[(CH₃)₂NCONH]—C₆H₃ | H | Cl | Cl | 116–118 |
| 62 | CH₃ | CH₃ | C₆H₅ | H | Cl | Cl | |
| 63 | CH₃ | CH₃ | C₆H₅ | H | H | Cl | 88–90 |
| 64 | CH₃ | CH₃ | 3,5-Cl₂—C₆H₃ | H | Cl | Cl | 87–89 |
| 65 | CH₃ | CH₃ | 3,5-Cl₂—C₆H₃ | H | CF₃ | H | |
| 66 | CH₃ | OCH₃ | 3,5-Cl₂—C₆H₃ | H | CF₃ | H | |
| 67 | CH₃ | OCH₃ | 3,5-Cl₂—C₆H₃ | H | Cl | Cl | |
| 68 | CH₃ | CH₃ | 2-CH₃—4-Cl—5-i-C₃H₇—C₆H₂ | H | Cl | Cl | 1.5758 |
| 69 | CH₃ | CH₃ | 2-CH₃—4-Cl—5-i-C₃H₇—C₆H₂ | H | CF₃ | H | |
| 70 | CH₃ | OCH₃ | 2-CH₃—4-Cl—5-i-C₃H₇—C₆H₂ | H | Cl | Cl | |
| 71 | CH₃ | OCH₃ | 2-CH₃—4-Cl—5-i-C₃H₇—C₆H₂ | H | CF₃ | H | |
| 72 | CH₃ | CH₃ | 2-Cl—4,5-(CH₃)₂—C₆H₂ | H | Cl | Cl | 1.6038 |
| 73 | CH₃ | CH₃ | 2-Cl—4,5-(CH₃)₂—C₆H₂ | H | CF₃ | H | |
| 74 | CH₃ | OCH₃ | 2-Cl—4,5-(CH₃)₂—C₆H₂ | H | CF₃ | H | |
| 75 | CH₃ | CH₃ | 2,4-Cl₂—C₆H₃ | H | Cl | Cl | |
| 76 | CH₃ | CH₃ | 2,4-Cl₂—C₆H₃ | H | H | Cl | 1.6074 |
| 77 | CH₃ | CH₃ | 4-F—C₆H₄ | H | CF₃ | H | |
| 78 | CH₃ | CH₃ | 4-F—C₆H₄ | H | Cl | Cl | |
| 79 | CH₃ | CH₃ | 2,4-F₂—C₆H₃ | H | Cl | Cl | |
| 80 | CH₃ | CH₃ | 2,4-F₂—C₆H₃ | H | CF₃ | H | |
| 81 | CH₃ | CH₃ | 4-NO₂—C₆H₄ | H | Cl | Cl | 80–83 |
| 82 | CH₃ | CH₃ | 4-NO₂—C₆H₄ | H | H | Cl | 80–81 |
| 83 | CH₃ | CH₃ | C₆H₅ | H | H | F | 1.5825 |
| 84 | CH₃ | CH₃ | 4-Cl—C₆H₄ | H | H | Cl | 85–87 |
| 85 | CH₃ | CH₃ | 4-Cl—C₆H₄ | H | H | F | 1.5765 |
| 86 | CH₃ | CH₃ | —CH₂—C₆H₅ | H | Cl | Cl | |

The isoureas of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solution, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 8 is mixed with 10 parts by weight of N-methyl-alpha-pyrrolidone. A mixture is obtained which is suitable for application in the form of very fine drops.

II. 10 parts by weight of compound no. 28 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 39 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 50 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 40 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 41 is intimately mixed with 95 parts by weight of particulate kaolin. A dust is obtained containing 5% by weight of the active ingredient.

VII. 30 parts by weight of compound no. 42 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 15 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combatted and their growth stage, and varies from 0.05 to 5 kg/ha, but is preferably from 0.25 to 3.0 kg/ha.

The herbicidal action of urea derivatives of the formula I on plant growth is demonstrated in greenhouse experiments.

The vessels employed were plastic flowerpots having a volume of 300 cm$^3$, and which were filled with a sandy loam containing about 3.0% humus. In the case of soybeans, peat was added for better growth. The seeds of the testplants were sown shallow, and separately, according to species.

For the preemergence treatment, the active ingredients were applied to the surface of the soil immediately after the seeds had been sown. The compounds were emulsified or suspended in water as vehicle, and sprayed through finely distributing nozzles. The application rates were 3.0 and 2.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredient.

For the postemergence treatment, the plants were first grown in the vessels to a height of from 3 to 15 cm, depending on growth form, before being treated. For this treatment, either plants which had been sown directly in the pots and grown there were selected, or plants which had been grown from seedlings and were transplanted to the pots a few days before treatment. The application rates for postemergence treatment varied, depending on the active ingredient, from 0.5 to 3.0 kg/ha. No covers were placed on the vessels in this method.

The pots were set up in the greenhouse—species from warmer areas at from 20° to 35° C., and species from moderate climates at 10° to 20° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plant species used in the experiments were Amaranthus spp., Amaranthus retroflexus, Arachis hypogaea, Cassia spp., Cassia tora, Chenopodium album, Desmodium tortuosum, Galium aparine, Glycine max., Gossypium hirsutum, Helianthus annuus, Ipomoea spp., Lamium amplexicaule, Lolium multiflorum, Mercurialis annua, Sesbania exaltata, Sida spinosa, Sinapis alba, Solanum nigrum, Sorghum halepense, Triticum aestivum, Abutilon theophrasti, Avena fatua, Digitaria sanguinalis, and Viola tricolor.

On preemergence application of 3.0 kg/ha of, for example, compounds nos. 3, 40, 11, 41, 1, 86, 46 and 38, a considerable herbicidal action was achieved. In this application method, compound no. 1, for instance, selectively combatted—at a rate of 2.0 kg/ha—unwanted plants in soybeans and wheat.

TABLE 1

Herbicidal action on preemergence application of 3.0 kg/ha in the greenhouse

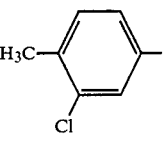

| Ex. no. | R¹ | R² | R³ | Lolium multiflorum | Sinapis alba |
|---|---|---|---|---|---|
| 3 | 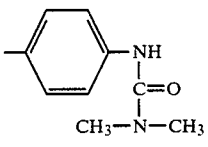 | —OCH₃ | 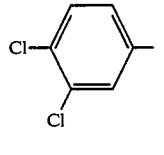 | 90 | 100 |
| 40 | 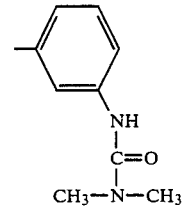 | —OCH₃ | 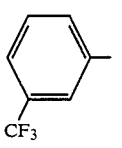 | 90 | 100 |
| 11 | 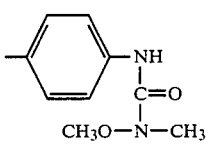 | CH₃ |  | 98 | 98 |

TABLE 1-continued

Herbicidal action on preemergence application of 3.0 kg/ha in the greenhouse

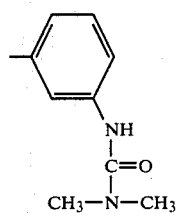

| Ex. no. | R¹ | R² | R³ | Lolium multiflorum | Sinapis alba |
|---|---|---|---|---|---|
| 41 | 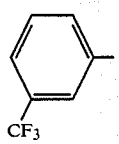 (3-CF₃-phenyl) | OCH₃ | 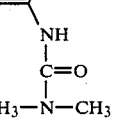 (phenyl-NH-C(=O)-N(CH₃)-CH₃) | 95 | 100 |
| 1 | 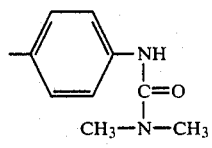 (3,4-di-Cl-phenyl) | CH₃ | 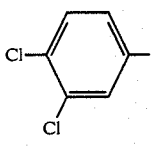 (phenyl-NH-C(=O)-N(CH₃)-CH₃) | 100 | 98 |
| 86 | 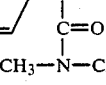 (3,4-di-Cl-phenyl) | CH₃ | —CH₂— 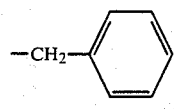 (benzyl) | 95 | 100 |
| 46 | 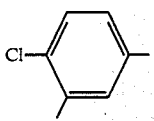 (3,4-di-Cl-phenyl) | OCH₃ | 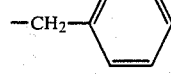 (4-methyl-phenyl-NHC(=O)-N(CH₃)₂) | 100 | 100 |
| 38 | 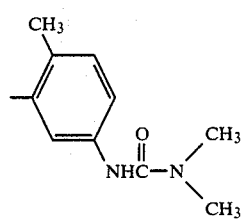 (3,4-di-Cl-phenyl) | OCH₃ | 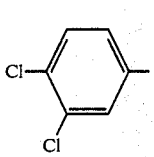 (phenyl-NHCOCH₃) | 100 | 100 |

On postemergence application of 3.0 kg/ha, compounds nos. 9, 45, 46, 2, 11, 20, 21, 27, 13, 38 and 37 had a herbicidal action on Ipomoea spp. and the grass *Lolium multiflorum* used by way of example. Compound no. 8 had a selective action at a rate of 1.0 kg/ha in crops such as groundnuts and cotton. Cassia spp. (*Cassia tora* and *Cassia obtusiflora*) can be controlled in soybeans with compound no. 39 at a rate of 1.0 kg/ha. Further, for example compounds nos. 1, 8, 27, 49, 40, 46, 37 and 38 combatted broadleaved plants. The action of compounds nos. 15, 14 and 40 at 1.0 kg/ha was typical on an unwanted grass species (*Sorghum halepense*) with selectivity in cotton. Compounds nos. 50, 58, 55, 56 and 33 have an action, on postemergence application of 0.5 kg/ha, on unwanted broadleaved plants. Compound no. 81 at 1.0 kg/ha, and compound no. 51 at 0.5 kg/ha had a selective herbicidal action when applied postemergence.

TABLE 2

Selective control of unwanted broadleaved plants on preemergence application of 2 kg/ha of compound no. 1 in the greenhouse

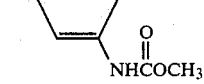

| Test plants | Damage (%) |
|---|---|
| Glycine max | 10 |
| *Triticum aestivum* | 0 |
| *Amaranthus retroflexus* | 100 |

TABLE 2-continued

Selective control of unwanted broadleaved plants on preemergence application of 2 kg/ha of compound no. 1 in the greenhouse

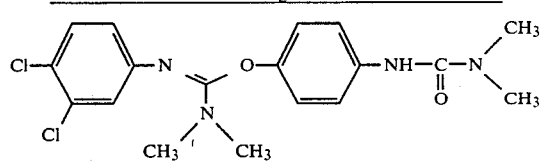

| Test plants | Damage (%) |
|---|---|
| Chenopodium album | 98 |
| Sinapis alba | 90 |
| Solanum nigrum | 98 |

TABLE 3

Herbicidal activity on postemergence application of 3 kg/ha in the greenhouse

| Ex. no. | R¹ | R² | R³ | Ipomoea spp. | Lolium multiflorum |
|---|---|---|---|---|---|
| 9 | 3,4-diCl-phenyl | OCH₃ | -C₆H₄-NH-C(O)-N(CH₃)(OCH₃) | 100 | 100 |
| 45 | 3,4-diCl-phenyl | CH₃ | 3-CH₃-4-(NH-C(O)-N(CH₃)₂)-phenyl | 95 | 98 |
| 46 | 3,4-diCl-phenyl | OCH₃ | 3-CH₃-4-(NH-C(O)-N(CH₃)₂)-phenyl | 100 | 100 |
| 2 | 3,4-diCl-phenyl | OCH₃ | -C₆H₄-NHCON(CH₃)₂ | 100 | 100 |
| 11 | 3-CF₃-phenyl | CH₃ | -C₆H₄-NHCON(CH₃)(OCH₃) | 100 | 100 |
| 20 | 3,4-diCl-phenyl | CH₃ | -C₆H₄-NHCOOC₂H₅ | 100 | 100 |
| 21 | 3,4-diCl-phenyl | OCH₃ | -C₆H₄-NHCOOC₂H₅ | 100 | 98 |

TABLE 3-continued

Herbicidal activity on postemergence application of 3 kg/ha in the greenhouse

| Ex. no. | R¹ | R² | R³ | Test plants and % damage Ipomoea spp. | Lolium multiflorum |
|---|---|---|---|---|---|
| 27 | 3-Cl-4-CH₃-phenyl | OCH₃ | 4-[O-CH(CH₃)-COOCH₃]-phenyl | 95 | 100 |
| 13 | 4-CH₃-phenyl-CH₂-CH₂-O-(4-phenyl) | OCH₃ | 4-[NHCON(CH₃)(OCH₃)]-phenyl | 100 | 95 |
| 38 | 3,4-diCl-phenyl | OCH₃ | 3-NHCOOCH₃-phenyl | 100 | 100 |
| 37 | 3,4-diCl-phenyl | CH₃ | 3-NHCOOCH₃-phenyl | 100 | 100 |

TABLE 4

Selective control of unwanted broadleaved plants on postemergence application of 1 kg/ha of compound no. 8 in the greenhouse Structure: 3,4-diCl-C₆H₃—N=C(—N(CH₃)₂)—O—C₆H₄—NH—C(=O)—N(CH₃)(OCH₃)

| Test plants | Damage (%) |
|---|---|
| *Arachis hypogaea* | 5 |
| *Gossypium hirsutum* | 9 |
| *Amaranthus* spp. | 100 |
| *Cassia tora* | 95 |
| *Ipomoea* spp. | 89 |
| *Chenopodium album* | 100 |
| *Desmodium tortuosum* | 100 |
| *Sesbania exaltata* | 100 |
| *Sida spinosa* | 89 |

TABLE 5

Selective control of broadleaved weeds on postemergence application of 1 kg/ha of compound no. 27 in the greenhouse Structure: 3-Cl-4-CH₃-C₆H₃—N=C(—N(CH₃)(OCH₃))—O—C₆H₄—O—CH(CH₃)—COOCH₃

| Test plants | Damage (%) |
|---|---|
| *Gossypium hirsutum* | 0 |
| *Helianthus annuus* | 10 |
| *Triticum aestivum* | 10 |

TABLE 5-continued

Selective control of broadleaved weeds on postemergence application of 1 kg/ha of compound no. 27 in the greenhouse

| Test plants | Damage (%) |
|---|---|
| *Chenopodium album* | 100 |
| *Lamium amplexicaule* | 100 |

TABLE 6

Control of broadleaved weeds in groundnuts; postemergence application of 1 kg/ha of compound no. 49

Structure: 3,4-diCl-C₆H₃—N=C(—N(CH₃)₂)—O—C₆H₄—NH—C(=O)—cyclopropyl

| Test plants | Damage (%) |
|---|---|
| *Arachis hypogaea* | 0 |
| *Desmodium tortuosum* | 100 |
| *Lamium amplexicaule* | 100 |
| *Mercurialis annua* | 100 |
| *Sesbania exaltata* | 100 |

TABLE 7

Selective control of Cassia spp. in soybeans on

TABLE 7-continued postemergence application of 1 kg/ha of compound no. 39 in the greenhouse

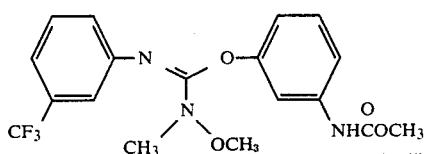

TABLE 7-continued

| Test plants and % damage | |
|---|---|
| Glycine max | Cassia spp. |
| 0 | 100 |

TABLE 8

Control of unwanted broadleaved plants in sunflowers on postemergence application in the greenhouse of 1 kg/ha $$R-N=C(-O-R^3)(-N(CH_3)(R^2))$$

| Ex. no. | R | R² | R³ | Test plants and % damage | | |
|---|---|---|---|---|---|---|
| | | | | Helianthus annuus | Chenopodium album | Galium aparine |
| 37 | 3,4-Cl₂-C₆H₃- | CH₃ | 3-(NHCOOCH₃)-C₆H₄- | 10 | 100 | |
| 40 | 3,4-Cl₂-C₆H₃- | OCH₃ | 3-(NHCON(CH₃)₂)-C₆H₄- | 10 | 100 | |

TABLE 9

Selective control of broadleaved weeds in cotton; postemergence application in the greenhouse of 1 kg/ha $$R-N=C(-O-R^3)(-N(CH_3)(R^2))$$

| Ex. no. | R | R² | R³ | Test plants and % damage | | |
|---|---|---|---|---|---|---|
| | | | | Gossypium hirsutum | Amaranthus retroflexus | Cassia spp. |
| 46 | 3,4-Cl₂-C₆H₃- | OCH₃ | 4-CH₃-3-(NHCON(CH₃)₂)-C₆H₃- | 10 | 100 | 100 |
| 37 | 3,4-Cl₂-C₆H₃- | CH₃ | 3-(NHCOOCH₃)-C₆H₄- | 0 | 100 | 100 |

TABLE 9-continued

Selective control of broadleaved weeds in cotton;
postemergence application in the greenhouse of 1 kg/ha

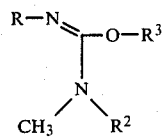

| Ex. no. | R | R² | R³ | Gossypium hirsutum | Amaranthus retroflexus | Cassia spp. |
|---|---|---|---|---|---|---|
| 38 | 3,4-Cl₂-C₆H₃- | OCH₃ | -C₆H₄-NHCOOCH₃ | 0 | 100 | 100 |

TABLE 10

Control of *Sorghum halepense* as an example of a grassy weed on
postemergence application of 1 kg/ha in the greenhouse

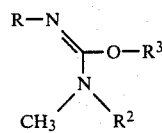

| Ex. no. | R | R² | R³ | Gossypium hirsutum | Sorghum halepense |
|---|---|---|---|---|---|
| 15 | 3,4-Cl₂-C₆H₃- | OCH₃ | -C₆H₄-NHCOC₂H₅ | 5 | 95 |
| 14 | 3,4-Cl₂-C₆H₃- | CH₃ | -C₆H₄-NHCOC₂H₅ | 0 | 100 |
| 40 | 3,4-Cl₂-C₆H₃- | OCH₃ | -C₆H₄-NHCON(CH₃)₂ | 0 | 100 |

TABLE 11

Herbicidal activity of various compounds on postemergence application in the greenhouse of 0.5 kg/ha

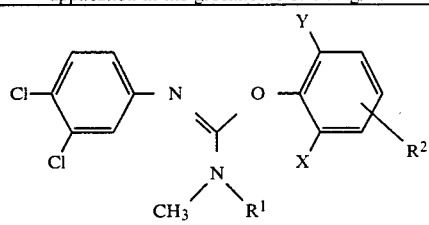

| Compound no. | R¹ | X | Y | R² | Position | Cassia tora | Galium aparine | Ipomoea spp. | Sinapis alba | Solanum nigrum |
|---|---|---|---|---|---|---|---|---|---|---|
| 50 | CH₃ | Cl | H | NHCN(CH₃)(OCH₃), ‖O | 4 | 100 | 90 | 100 | 80 | 100 |
| 58 | CH₃ | Cl | Cl | NHCN(CH₃)(OCH₃), ‖O | 4 | 100 | 80 | 100 | 100 | 85 |
| 55 | CH₃ | H | CH₃ | NHCN(CH₃)(OCH₃), ‖O | 3 | 100 | 90 | 100 | 90 | 100 |
| 56 | OCH₃ | H | CH₃ | NHCN(CH₃)(OCH₃), ‖O | 3 | 95 | 85 | 100 | 100 | 100 |
| 33 | CH₃ | H | H | —OCH₃ | 4 | 100 | 100 | 80 | 90 | 90 |

TABLE 12

Selective control of unwanted grasses and weeds on postemergence application of 1 kg/ha of compound no. 81 in the greenhouse

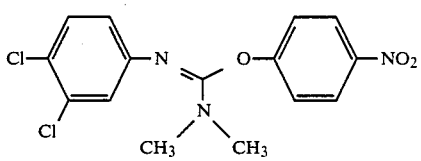

| Test plants | Damage (%) |
|---|---|
| Gossypium hirsutum | 0 |
| Helianthus annuus | 10 |
| Avena fatua | 90 |
| Chenopodium album | 100 |
| Digitaria sanguinalis | 90 |
| Galium aparine | 80 |
| Lamium amplexicaule | 100 |
| Viola tricolor | 100 |

TABLE 13

Control of broadleaved weeds in soybeans; postemergence application of 0.5 kg/ha of compound no. 51 in the greenhouse

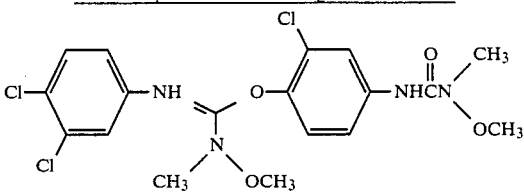

| Test plants | Damage (%) |
|---|---|
| Glycine max | 10 |
| Abutilon theophresti | 80 |
| Amaranthus retroflexus | 100 |
| Cassia tora | 100 |
| Ipomoea spp. | 100 |
| Sinapis alba | 100 |

In view of the numerous application methods possible, the compounds according to the invention (or agents containing them) can be used in a large number of crops for removing unwanted plants. The following crops may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |

-continued

| Botanical name | Common name |
|---|---|
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize (post-directed) |

To increase the spectrum of action and to achieve synergistic effects, the novel substituted isoureas may be mixed among themselves, or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

A number of active ingredients which, when combined with the isoureas of the formula I, give mixtures suitable for use in various fields are given below by way of example:

3-(1-methylethyl)-1H-2,1,3-benzothiadiazin-4(3H)-one-2,2-dioxide and salts 3-(1-methylethyl)-8-chloro-1H-2,1,3-benzothiadiazin-4(3H)-one-2,2-dioxide and salts 3-(1-methylethyl)-8-fluoro-1H-2,1,3-benzothiadiazin-4(3H)-one-2,2-dioxide and salts 3-(1-methylethyl)-8-methyl-1H-2,1,3-benzothiadiazin-4(3H)-one-2,2-dioxide and salts 1-methoxymethyl-3-(1-methylethyl)-2,1,3-benzothiadiazin-4-(3H)-one-2,2-dioxide 1-methoxymethyl-8-chloro-3-(1-methylethyl)-2,1,3-benzothiadiazin-4(3H)-one-2,2-dioxide 1-methoxymethyl-8-fluoro-3-(1-methylethyl)-2,1,3-benzothiadiazin-4(3H)-one-2,2-dioxide 1-cyano-8-chloro-3-(1-methylethyl)-2,1,3-benzothiadiazin-4(3H)-one-2,2-dioxide 1-cyano-8-fluoro-3-(1-methylethyl)-2,1,3-benzothiadiazin-4(3H)-one-2,2-dioxide 1-cyano-8-methyl-3-(1-methylethyl)-2,1,3-benzothiadiazin-4(3H)-one-2,2-dioxide 1-azidomethyl-3-(1-methylethyl)-2,1,3-benzothiadiazin-4(3H)-one-2,2-dioxide 3-(1-methylethyl)-1H-pyridino-[3,2-e]-2,1,3-thiadiazin-(4)-one-2,2-dioxide N-(1-ethylpropyl)-2,6-dinitro-3,4-dimethylaniline N-(1-methylethyl)-N-ethyl-2,6-dinitro-4-trifluoromethylaniline N-n-propyl-N-β-chloroethyl-2,6-dinitro-4-trifluoromethylaniline N-n-propyl-N-cyclopropylmethyl-2,6-dinitro-4-trifluoromethyl-aniline N,N-di-n-propyl-2,6-dinitro-3-amino-4-trifluoromethylaniline N,N-di-n-propyl-2,6-dinitro-4-methylaniline N,N-di-n-propyl-2,6-dinitro-4-methylsulfonylaniline N,N-di-n-propyl-2,6-dinitro-4-aminosulfonylaniline N,N-di-β-chloroethyl-2,6-dinitro-4-methylaniline N-ethyl-N-(2-methylallyl)-2,6-dinitro-4-trifluoromethylaniline 3,4-dichlorobenzyl N-methylcarbamate 2,6-di-tert.butyl-4-methylphenyl N-methylcarbamate isopropyl N-phenylcarbamate isopropyl N-3-chlorophenylcarbamate but-1-yn-3-yl N-3-chlorophenylcarbamate 4-chlorobut-2-yn-1-yl N-3-chlorophenylcarbamate methyl N-3,4-dichlorophenylcarbamate methyl N-(4-aminobenzenesulfonyl)-carbamate 0-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
ethyl-N-[3-N'-(3-chloro-4-fluorophenylcarbamoyloxy)-phenyl]-carbamate
ethyl-N-[3-N'-(3,4-difluorophenylcarbamoyloxy)-phenyl]-carbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-ethylhexahydro-1-H-azepine-1-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
alpha,alpha-dichloropropionic acid, sodium salt
alpha,alpha-dichlorobutyric acid, sodium salt
alpha,alpha,beta,beta-tetrafluoropropionic acid, sodium salt
alpha-methyl-alpha,beta-dichloropropionic acid, sodium salt
methyl alpha-chloro-beta-(4-chlorophenyl)-propionate
methyl alpha,beta-dichloro-beta-phenylpropionate benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-(3,4-dichlorophenyl)-amino)-propionate
methyl 2-(N-benzoyl-3-chloro-4-fluorophenylamino)-propionate isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
-chloro-4,6-bisethylamino-1,3,5-triazine
-chloro-4,6-bisisopropylamino-1,3,5-triazine
-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-isopropyl-5-bromo-6-methyluracil
3-sec.butyl-5-bromo-6-methyluracil
3-cyclohexyl-5,6-trimethyleneuracil
2-methyl-4-(3'-trifluoromethylphenyl)-tetrahydro-1,2,4-oxa-diazine-3,5-dione
2-methyl-4-(4'-fluorophenyl)-tetrahydro-1,2,4-oxadiazine-3,5-dione
3-amino-1,2,4-triazole
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(pyrazolyl-methyl)-2-chloroacetanilide
2,6-dimethyl-N-(pyrazolyl-methyl)-2-chloroacetanilide
2,6-dimethyl-N-(4-methylpyrazolyl-methyl)-2-chloroacetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-(n-butoxymethyl)-2-chloroacetanilide
2,6-diethyl-N-ethoxycarbonylmethyl-2-chloroacetanilide
2,3-dimethyl-N-isopropyl-2-chloroacetanilide 2,6-diethyl-N-(2-n-propoxyethyl)-2-chloroacetanilide
alpha-(2-methyl-4-chlorophenoxy)-N-methoxyacetamide p0 2-(alpha-naphthoxy)-N,N-diethylpropionamide
2,2-diphenyl-N,N-dimethylacetamide
alpha-(3,4,5-tribromopyrazol-1-yl)-N,N-dimethylpropionamide
N-(1,1-dimethylprop-2-ynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
2-acetamido-2,4-dimethyltrifluoromethanesulfone anilide
2-acetamido-4-methyltrifluoromethanesulfone anilide
2-propionylamino-4-methyl-5-chlorothiazole
O-(methylaminosulfonyl)-glycolic acid hexamethylene imide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
3-(4-bromophenyl)-3,4,5,9,10-pentaazatetracyclo-[5,4,1,O$^{2,6}$,O$^{8,1}$]-dodeca-3,9-diene
2-ethoxy-2,3-dihydro-3,3-dimethyl-5-benzofuranylmethane sulfonate
2-methyl-4,6-dinitrophenol (salts, esters)
3-(4-chlorophenyl)-3,4,5,9,10-pentaazatetracyclo-[5,4,1,O$^{2,6}$,O$^{8,1}$]-dodeca-3,9-diene
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(alpha,alpha-dimethylbenzyl)-3-(4-methylphenyl)-urea
1-phenyl-3-(2-methylcyclohexyl)-urea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-3-methyl-3-n-butylurea
1-(4-isopropylphenyl)-3,3-dimethylurea
1-(3-trifluoromethylphenyl)-3,3-dimethylurea
1-(alpha,alpha-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea imidazolidin-2-one-1-carboxylic acid isobutylamide
1,2-dimethyl-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2,4-dichlorophenoxyacetic acid (salts, esters, amides)
2-methyl-4-chlorophenoxyacetic acid (salts, esters, amides)
3,5,6-trichloro-2-pyridinyl-oxyacetic acid (salts, esters, amides)
methyl alpha-naphthoxyacetate
2-(2,4-dichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite O,O-diisopropyl-5-(2-benzosulfonylaminoethyl)-phosphorodithioate
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxyamino)-butylidene]-5-(2-ethylthiopropyl)-3-hydroxy-cyclohex-2-en-1-one (salts)
2-[1-(N-ethoxyamino)-butylidene]-5-(2-phenylthiopropyl)-3-hydroxy-cyclohex-2-en-1-one (salts)
ethyl 4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-alpha,alpha,beta-trifluoro-beta-bromoethoxyphenyl)-3-(2H)-pyridazinone
2,4-dichloro-3'-[2-(2-ethoxy-ethoxy)-ethoxy]-4'-nitrodiphenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide
1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1(-4-[2-(4-methylphenyl)-ethoxy]-phenyl)-3-methyl-3-methoxyurea
2,6-dimethyl-N-(pyrazol-methylenoxymethyl)-2-chloroacetanilide
2-methyl-6-ethyl-N-(pyrazolyl-methylenoxymethyl)-2-chloroacetanilide
alpha-2,4-dichlorophenoxy-propionic acid)-(3-methoxycarbonyl-amino)-anilide
1-(alpha-2-bromo-4-chlorophenoxypropionic acid)-3-(O-methylcarbamoyl)-anilide
2-methyl-6-ethyl-N-(pyrazolyl-ethylenoxymethyl)-2-chloroacetanilide
2-(3-trifluoromethylphenyl)-4H-3,1-benzoxazin-4-one
2-(3-pentafluoroethoxyphenyl)-4H-3,1-benzoxazin-4-one
2-(3-trifluoromethylthio-phenyl)-4H-3,1-benzoxazin-4-one
2-(3-difluorochloromethoxyphenyl)-4H-3,1-benzoxazin-4-one
5-nitro-2-(3-trifluoromethyl-phenyl)-4H-3,1-benzoxazin-4-one
5-chloro-2-(3-trifluoromethoxyphenyl)-4H-3,1-benzoxazin-4-one
5-chloro-2-(3-alpha,alpha,beta,beta-tetrafluoroethoxyphenyl)-4H-3,1-benzoxazin-4-one
5-fluoro-2-(3-alpha,alpha,beta,beta-tetrafluoroethoxyphenyl)-4H-3,1-benzoxazin-4-one
5-chloro-2-(4-difluorochloromethoxyphenyl)-4H-3,1-benzoxazin-4-one
5-fluoro-2-(4-difluorochloromethoxyphenyl)-4H-3,1-benzoxazin-4-one
5-fluoro-2-phenyl-4H-3,1-benzoxazin-4-one
5-fluoro-2-(3-difluoromethoxyphenyl)-4H-3,1-benzoxazin-4-one
5-chloro-2-phenyl-4H-3,1-benzoxazin-4-one
methyl N-3-chloro-4-isopropylphenyl-thiolcarbamate
6-methyl-3-methoxy-5,6-dihydro-1,2,4,6-thiatriazin-5-one-1,1-dioxide, sodium salt
6-methyl-3-ethoxy-5,6-dihydro-1,2,4,6-thiatriazin-5-one-1,1-dioxide
5-amino-4-chloro-2-phenyl-3(2H)-pyridazinone
5-amino-4-bromo-2-phenyl-3(2H)-pyridazinone
5-methylamino-4-chloro-2-(3-trifluoromethylphenyl)-3(2H)-pyridazinone
5-methylamino-4-chloro-2-(3-alpha,alpha,beta,beta-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
1-[3'-(2''-chloro-4''-trifluoromethylphenoxy)]-phenyl-4,5-dimethoxy-pyridazin-6-one
1-[4'-(3''-trifluoromethyl-phenoxy)]-phenyl-4,5-dimethoxypyridazin-6-one
methyl N-[4-(4'-methoxy-phenoxy)-3-chlorophenyl]-carbamate
methyl N-[4-(4'-difluoromethoxy-phenoxy)-3-chlorphenyl]-thio-carbamate
methyl N-[4-(4'-difluoromethoxy-phenoxy)-phenyl]thiocarbamate
1-[4-(4'-methylphenylpropyl)-phenyl]-3-methyl-3-methoxyurea
1-[3-(4'-chlorophenyl-propyl)-phenyl]-3-methyl-3-methoxyurea
1-[4-(3-phenyl-2-methyl-propyl)-phenyl]-3-methyl-3-methoxyurea
1-[4-(3-(4'-chlorophenyl)-2-methyl-propyl)-phenyl]-3-methyl-3-methoxyurea
1-[4-(3-(4'-methylphenyl)-2-methylpropyl)-phenyl]-3--methyl--3-methoxyurea
2-[1-(N-ethyloxyamino)-butylidene]-5-(4-ethylphenyl)-3-hydroxy-cyclohexen-(2)-one-(1) (salts)
2-[1-(N-ethyloxyamino)-butylidene]-5-(4-fluorophenyl)-3-hydroxy-cyclohexen-(2)-one-(1) (salts)
2-[1-(N-ethyloxyamino)-butylidene-5-(4-chlorophenyl)--3--hydroxy-cyclohexen-(2)-one-(1) (salts)
methyl 2'-(2,4,6-trichlorophenyl)-hydrazino-2-cyanoacrylate
2-[1-(N-ethyloxyamino)-butylidene]-5-(1,3,3-trimethyl-cyclohexen-1-yl-2)-3-hydroxy-cyclohexen-(2)-one-(1) (salts)
2-[1-(N-ethyloxyamino)-butylidene]-5-(2,4,4-trimethyl-cyclohexen-1-yl-3)-3-hydroxy-cyclohexen-(2)-one-(1) (salts)

2-[1-(N-3-chloroallyl-oxamino)-butylidene]-5-(1-methylcyclohex-1-en-4-yl)-3-hydroxy-cyclohexen-(2)-one-(1) (salts)
3-isobutoxy-5-methyl-4-methoxycarbonyl-pyrazole
5-amino-1-(2,4,6-trichlorophenyl)-4-cyano-pyrazole
5-amino-1-(2,4,6-tribromophenyl)-4-cyano-pyrazole
5-amino-1-(2,4,6-trichlorophenyl)-4-methoxycarbonyl-pyrazole
5-amino-(2,4-dichloro-6-bromophenyl)-4-methoxycarbonyl-pyrazole
5-amino-(2,6-dichloro-4-bromophenyl)-4-methoxycarbonyl-pyrazole
5-chloro-2-(3-trifluoromethyl-phenyl)-4H-3,1-benzoxazin-4-one
5-fluoro-2-(3-trifluoromethyl-phenyl)-4H-3,1-benzoxazin-4-one
2-(3-tetrafluoroethoxyphenyl)-4H-3,1-benzoxazin-4-one
5-chloro-2-(4'-fluorophenyl)-4H-3,1-benzoxazin-4-one
5-fluoro-2-(4'-fluorophenyl)-4H-3,1-benzoxazin-4-one
5-fluoro-2-(3'fluorophenyl)-4H-3,1-benzoxazin-4-one
5-chloro-2-(3'-fluorophenyl)-4H-3,1-benzoxazin-4-one
5-chloro-2-(3'-difluorochlormethylphenyl)-4H-3,1-benzoxazin-4-one
5-fluoro-2-(3'-difluorochlormethylphenyl)-4H-3,1-benzoxazin-4-one
6-methyl-3-methoxy-5-(4'-nitrophenoxy)-6H-1,2,4,6-thiatriazine-1,1-dioxide
6-methyl-3-methoxy-5-(propargyloxy-6H-1,2,4,6-thiatriazine-1,1-dioxide
6-methyl-3-methoxy-5-(2,4-dichlorobenzoxy)-6H-1,2,4,6-thiatriazine-1,1-dioxide
2-(2',4'-dichlorophenoxy)-2-fluoropropionic acid (salts, esters)
butyl 2-[4-(5'-trifluoromethylpyridyl-2-oxy)-phenoxy]-propionate
2-[4-(3'-chloro-5'-trifluoromethylpyridyl-2-oxy)-phenoxy]-propionic acid (salts, esters)
pentyl 2-[4-(6-chloroquinoxalyl-2-oxy)-phenoxy]-propionate
methyl 2-[4-(6-chloroquinoxalyl-2-oxy)-phenoxy]-propionate
2-[4-(6-chlorobenzthiazolyl-2-oxy)-phenoxy]-propionic acid (salts, esters)
2-[4-(6-chlorobenzoxazolyl-2-oxy)-phenoxy]-propionic acid (salts, esters)
1-[5-(3-fluorobenzylthio)-thiadiazolyl-2]-1-methylurea
2-methoxycarbonyl-N-(3,5-dimethylpyrimidinyl-2-aminocarbonyl)-benzole sulfonamide
alpha-(3,5,6-trichloropyrid-2-yl-oxy)-acetic acid (salts, esters)
alpha-(4-amino-3,5-dichloro-6-fluoro-pyrid-2-yl-oxy)-acetic acid (salts, esters)
S-[N-(4-chlorophenyl)-N-isopropyl-carbamoyl-methyl]-O,O-dimethyl-dithiophosphate
ammonium-(3-amino-3-carboxy-propyl)-methylphosphinate
(hydroxy)-(methyl)-phosphinyl-L-alpha-aminobutyryl-L-alanyl, sodium salt
4-trifluoromethyl-diphenyl ether
2-(3,5-dichlorophenyl)-2-(2'2'2'-trichloroethyl)-oxirane
2,4-diamino-5-methylthio-6-chloropyrimidine
N-(4-ethylthio-2-trifluoromethyl-phenyl)-methylsulfonamide
3-methoxy-4-methyl-5-(3-methyl-2-butenyloxy)-1,2-di(-hydroxymethyl)-benzole
2-(3,5-dimethylphenoxy)-2-(1,2,4-triazolyl-1)-acetic acid-N-tert-butylamide
2-(3,5-dichlorophenoxy)-2-(1,2,4-triazolyl-1)-acetic acid-N-tert-butylamide
3,7-dichloro-8-quinolinecarboxylic acid (salts, esters)
5-(2-chloro-4-trifluoromethyl-phenoxy)-N-(1-methoxycarbonylethoxy)-benzamide
N-[3-(1-ethyl-1-methylpropyl)-isoxazolyl-5]-2,6-dimethoxybenzamide
2'-methoxyethyl-2-[5-(2-chloro-4-trifluoromethyl-phenoxy)-2-nitrophenoxy]-propionate
methyl-6-(4-isopropyl-4-methyl-5-oxo-2-imidazolin-2-yl)-3-methylbenzoate
methyl-6-(4-isopropyl-4-methyl-5-oxo-2-imidozin-2-yl)-4-methylbenzoate
benzyltrimethylammonium chloride
1-[alpha-(4-trifluoromethyl-phenoxy)-phenoxy-propionic acid]-3-(O-methylcarbamoyl)-anilide
1-dodecyl-cycloheptan-2-one
N-[2-chloro-4-methylsulfonyl-phenyl]-chloromethanesulfonamide
N-[2-bromo-4-ethylsulfonyl-phenyl]-chloromethanesulfonamide
N-[2,3-dichloro-4-(ethylsulfonyl)-phenyl]-chloromethanesulfonamide
2-[1-(N-ethoxyamino)-pyropylidene]-5-(pyrid-3-yl)-3-hydroxy-cyclohex-2-en-1-one (salts)
2,4,5-trichlorophenoxyacetic acid (salts, esters, amides)
2-[1-(N-ethoxyamino)-butylidene]-5-(tetrahydropyran-3-yl)-3-hydroxy-cyclohex-2-en-1-one (salts)
2-[1-(N-ethoxyamino)-butylidene]-5-(4-methyl-tetrahydropyran-3-yl)-3-hydroxy-cyclohex-2-en-1-one (salts)
2-[1-(N-ethoxyamino)-butylidene]-5-(tetrahydrotiopyran-3-yl)-3-hydroxy-cyclohex-2-en-1-one (salts)
2-[1-(N-ethoxyamino)-propylidene]-5-(pyrid-3-yl)-3-hydroxycyclohex-2-en-1-one (salts)
2-[1-(N-allyloxyamino)-butylidene]-5-(pyrid-3-yl)-3-hydroxy-cyclohex-2-en-1-one
2-[1-(N-ethoxyamino)-butylidene]-5-(pyrid-3-yl)-3-hydroxycyclohex-2-en-1-one (salts)
2-[1-(N-allyloxyamino)-butylidene]-5-(pyrid-3-yl)-3-hydroxy-cyclohex-2-en-1-one (salts)
2-[4,5-dihydro-4-methyl-4-isopropyl-5-oxo-1H-imidazol-2-yl]-3-quinolinecarboxylic acid
2-[4,5-dihydro-4-methyl-4-isopropyl-5-oxo-1H-imidazol-2-yl]-nicotinic acid, isopropylamine salt
2-chloro-2'-methyl-6'-ethyl-N-(N'-1-methoxycarbonyl)-ureidomethylacetanilide
2-chloro-2'-6'-diethyl-N-(N'-1-methoxycarbonyl)-ureidomethylacetanilide
2-chloro-2'-6'-dimethyl-N-(N'-1-methoxycarbonyl)-ureidomethylacetanilide
2-chloro-6-nitro-3-phenoxy-anilide
N-phosphonomethyl-glycine-trimethylsulfonium salt
5-(2-chloro-4-trifluoromethyl-phenoxy)-2-nitro-N-methansulfonyl-benzamide
1-ethoxycarbonyl-ethyl-5-(2-chloro-4-trifluoromethyl-phenoxy)-2-nitro-benzoate
1-[3'-(2''-chloro-4''-trifluoromethyl-phenyl-thio)-phenyl]-4,5-dimethoxy-pyridaz-6-one
3-methyl-6-fluoro-5H-thiazolo[2,3-b]-quinazolin-5-one
3-methyl-2-sulfonic acid-5H-thiazolo[2,3-b]-quinazolin-5-one
3-methyl-2-bromo-5H-thiazolo[2,3-b]-quinazolin-5-one
5H-triazolo[2,3-b]-quinazolin-5-one
2-(1-ethoxyamino-butylidene)-5-cyclododeca-1,5-dion-9-yl-cyclohex-1-en-1-one 2-(1-ethoxyamino-butylidene)-5-cyclododecyl-cyclohex-1-en-1-one (2-trimethylsilylethyl)-5-(4'-trifluoromethyl-2'-chloro-phenoxy)-2-nitro-benzylthioacetate 2-(2-chlorobenzyl)-4,4-dimethyl-isoxazolidin-3-one N-[4-(3,4-dichlorobenzyloxymethyl)-phenyl]-N'-methyl-N'-methoxyurea N-[4-(4-trifluoromethylbenzyloxymethyl)-phenyl]-N'-methyl-N'-methoxyurea N-[3-chloro-4-(1-benzyloxyethyl)-phenyl]-N'-methyl-N'-methoxyurea N-[4-(4-trifluoromethylbenzyloxyethyl)-phenyl]-N',N'-dimethylurea 3-(2'-chloro-4'-trifluoromethylphenoxy)-6-nitro-benzoic acid-N-methyl-sulfenamide isopropyl-3-(2'-chloro-4'-trifluoromethylphenoxy)-6-nitro-benzenesulfenate 1-methyl-4-isopropyl-2-(2-methylbenzyloxy)-exo-7-oxabicyclo-[2.2.1]heptane methyl 5-(2-chloro-4-trifluoromethylphenoxy)-2-nitro-acetophenoneoxime-O-acetate O-(3-phenyl-6-chloropyridazin-4-yl)-S-n-octyl-thiolcarbonate 3-methyl-7-chloroquinoline-8-carboxylic acid (salts, esters)

3-ethyl-7-chloroquinoline-8-carboxylic acid (salts, esters)

2,6-diethyl-N-(but-2-ynyl)-2-chloroacetanilide 2-chloro-4-trifluoromethyl-3'-[3''-carboxy-propionyl)-hydrazino]-4'nitro-diphenylether (sodium salt)

N-[(4-chloro-6-methoxy-pyrimidin-2-yl)-aminocarbonyl]-2-ethoxycarbonyl-benzene sulfonamide N-[(4-methoxy-6-methyl-1,3,5-triazin-2-yl)-aminocarbonyl]-2-methoxy-carbonyl-benzene sulfonamide 2-[1-(N-ethoxyamino)-butylidene]-5-(4a,7,8,8a-tetrahydro-2H,5H-pyrano[4,3-b]-pyran-3-yl)-3-hydroxy-cyclohexen-2-one 2-[1-(N-allyloxamino)-butylidene]-5-(4a,7,8,8a-tetrahydro-2H,5H-pyrano[4,3-b]-pyran-3-yl)-3-hydroxy-cyclohexen-2-en-1-one 2-[1-(N-allyloxamino)-butylidene]-5-(3,4,4a,7,8,8a-hexahydro-2H,5H-pyrano[4,3-b]-pyran-3-yl)-3-hydroxy-cyclohexen-2-en-1-one 2-[1-(N-ethoxyamino)-butylidene]-5-(3,4,4a,7,8,8a-hexahydro-2H,5H-pyrano[4,3-b]-pyran-3-yl)-3-hydroxy-cyclohexen-2-en-1-one 2-[4,5-dihydro-4-methyl-4-isopropyl-5-oxo-1H-imidazol-2-yl]-5-ethyl-pyridin-3-carboxylic acid 2-(1-ethoxyamino-butylidene)-5-(5,6-dihydro-2H-1,1-dioxo-thiopyran-3-yl)-3-hydroxy-cyclohex-2-en-1-one 2-(1-ethoxyamino-propylidene)-5-(5,6-dihydro-2H-1,1-dioxo-thiopyran-3-yl)-3-hydroxy-cyclohex-2-en-1-one 2-(1-propargylamino-butylidene)-5-(5,6-dihydro-2H-1,1-dioxothiopyran-3-yl)-3-hydroxy-cyclohex-2-en-1-one methyl 3-(2'-chloro-4'-trifluoromethylphenoxy)-6-nitro-phenylglyoxylate butyl 2-[4-(2-chloro-4-trifluoromethylphenoxy)-phenoxy]-propionate 2-carboxy-N-[[(4-methoxy-6-chloropyrimidin-2-yl)-amino]-carbonyl]-benzene sulfonamide It may also be useful to apply the isoureas of the formula I, either alone or in combination with other herbicides, in admixture with other crop protection agents, e.g., agents for combatting pests or phytopathogenic fungi or bacteria. The compounds may also be mixed with solutions of mineral salts used to remedy nutritional or trace element deficiencies. Non-phytotoxic oils and oil concentrates may also be added.

We claim:

1. An isourea of the formula

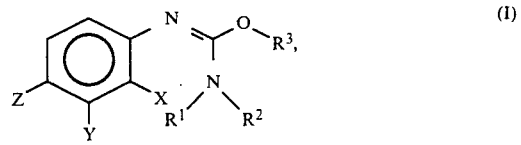

where X, Y and Z are identical or different and are each hydrogen, halogen, $C_1$–$C_4$-alkyl, $C_1$–$C_4$-alkoxy or $C_1$–$C_3$-haloalkyl, or are each phenoxy which is unsubstituted or substituted by halogen or $C_1$–$C_4$-alkyl, or are each aryl-$C_1$–$C_4$-alkoxy, where the aryl radical may be alkylated, $R^1$ is $C_1$–$C_3$-alkyl, $R^2$ is methoxy, $R^3$ is benzyl or is phenyl which can be monosubstituted or polysubstituted by $C_1$–$C_5$-alkyl, halogen, $C_1$–$C_4$-alkoxy, $C_1$–$C_3$-haloalkoxy, nitro, hydroxyl, $C_2$- or $C_3$-alkoxycarbonylmethoxy, 1-($C_2$- or $C_3$-alkoxycarbonyl)-ethoxy or a radical —NH—$R^4$, where $R^4$ is $C_2$–$C_4$-alkoxycarbonyl, $C_2$–$C_4$-alkylcarbonyl, $C_4$–$C_7$-cycloalkylcarbonyl, N-($C_1$–$C_4$-alkyl)-N-($C_1$–$C_4$-alkoxy)-aminocarbonyl, N,N-di-($C_1$–$C_4$-alkyl)-aminocarbonyl or $C_2$–$C_3$-alkoxycarbonyl-$C_1$–$C_4$-alkyl.

2. An isourea of the formula I as set forth in claim 1, where X is hydrogen.

3. An isourea of the formula I as set forth in claim 1, where X is hydrogen, $R^3$ is phenyl substituted by —NH$R^4$, where $R^4$ is N-($C_1$–$C_4$-alkyl)-N-($C_1$–$C_4$-alkoxy)-aminocarbonyl.

4. An isourea of the formula I as set forth in claim 1, where X is hydrogen, $R^1$ is methyl, $R^3$ chlorophenyl substituted by —NH$R^4$ and $R^4$ is N—(CH$_3$)—N—(OCH$_3$)—aminocarbonyl.

5. A herbicidal composition containing one or more inert additives and an effective amount of the formula I as set forth in claim 1.

6. A herbicidal composition containing one or more inert additives and an effective amount of an isourea of the formula I as set forth in claim 2.

7. A herbicide containing inert additives and from 0.1 to 95 wt % of an isourea of the formula I as set forth in claim 1.

8. A process for combatting the growth of unwanted plants, wherein the unwanted plants or the area to be kept free from unwanted plant growth are treated with a herbicidally effective amount of an isourea of the formula I as set forth in claim 1.

* * * * *